United States Patent [19]

Bergström et al.

[11] Patent Number: 5,545,187
[45] Date of Patent: Aug. 13, 1996

[54] MEDICAL FIELD DETECTOR AND TELEMETRY UNIT FOR IMPLANTS

[75] Inventors: Inga-Maria Bergström; Mats-Johan M. Bergström, both of Stockholm; Kenth Nilsson, Akersberga, all of Sweden

[73] Assignee: Pacesetter AB, Solna, Sweden

[21] Appl. No.: 391,957

[22] Filed: Feb. 21, 1995

[30] Foreign Application Priority Data

Feb. 23, 1994 [SE] Sweden .................................. 9400622

[51] Int. Cl.⁶ ................................................ A61N 1/37
[52] U.S. Cl. ................................................ 607/32
[58] Field of Search .................... 607/31, 32, 60; 128/903

[56] References Cited

U.S. PATENT DOCUMENTS

| | | | |
|---|---|---|---|
| 4,124,031 | 11/1978 | Mensink et al. . | |
| 4,203,447 | 5/1980 | Keller, Jr. et al. | 607/31 |
| 4,301,804 | 11/1981 | Thompson et al. . | |
| 4,453,162 | 6/1984 | Money et al. | 607/32 |
| 4,541,431 | 9/1985 | Ibrahim et al. . | |
| 4,586,508 | 5/1986 | Botina et al. | 607/32 |
| 4,944,299 | 7/1990 | Silvian | 607/32 |

FOREIGN PATENT DOCUMENTS 0530006  3/1993  European Pat. Off. .

OTHER PUBLICATIONS

"Elektrisk Mätteknik, Analoga instrument och mätmetoder," part 2, L. Grahm, Elektrisk mätteknik, Lund, Sweden, pp. 543–545.

Primary Examiner—William E. Kamm
Attorney, Agent, or Firm—Hill, Steadman & Simpson, A Professional Corp.

[57] ABSTRACT

A combined telemetry and magnetic field detector unit for use in a medical implant includes control logic, a magnetic field indicator, a telemetry circuit containing a number of switches, and a coil unit. The control logic is arranged to operate the switches such that switching between the telemetry function and the magnetic field detection function of the combined unit is achieved so the coil unit is utilized for transmission of telemetry signals to and from a programmer as well as for magnetic field detection. For magnetic field detection, the coil unit, which consists of multiple parts, is connected by the control logic such that the parts respectively form a primary side and a secondary side of a pulse transformer, with the magnetic field indicator connected by the control logic to the pulse transformer's secondary side.

12 Claims, 3 Drawing Sheets

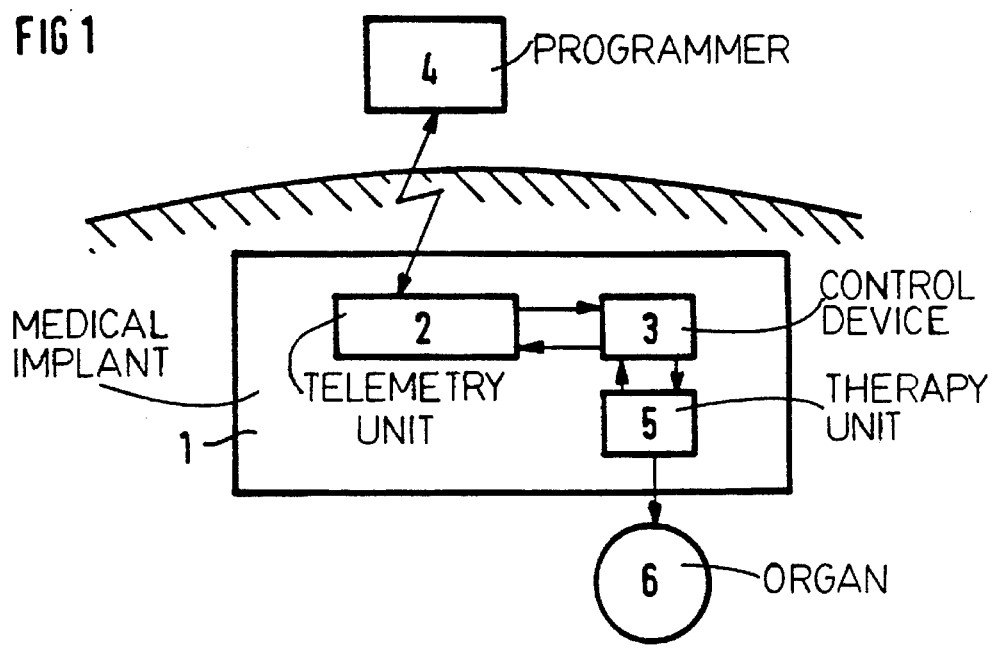
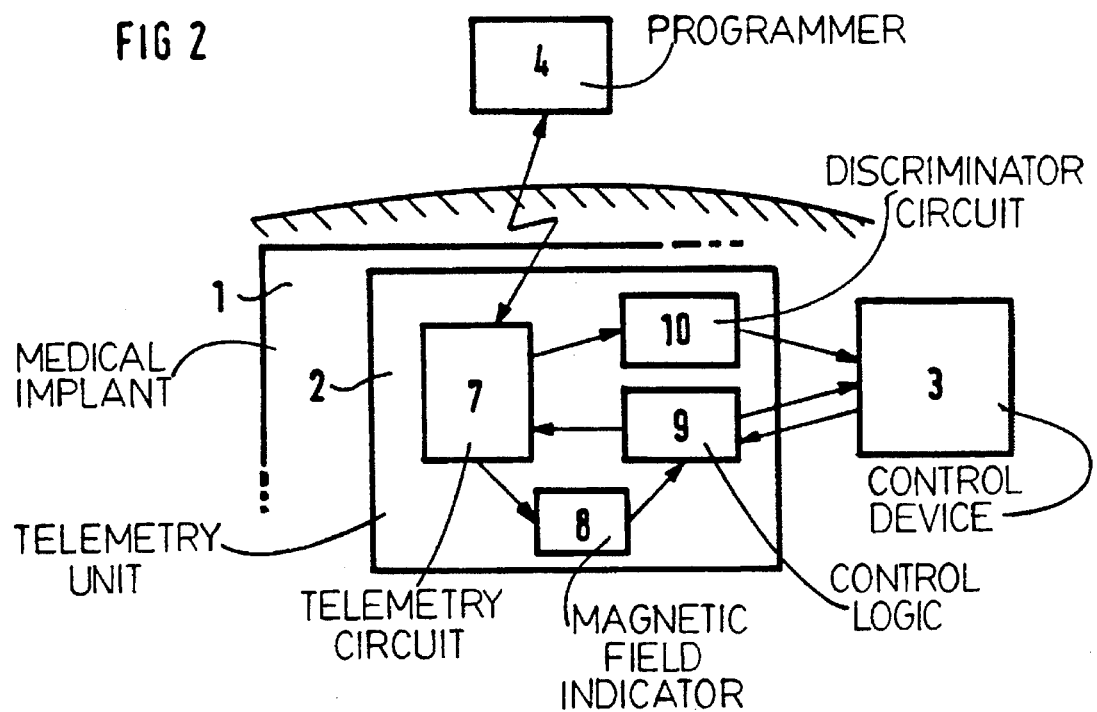

# 5,545,187

MEDICAL FIELD DETECTOR AND TELEMETRY UNIT FOR IMPLANTS

BACKGROUND OF THE INVENTION

1. Field of the Invention

The present invention relates generally to a medical implant, and specifically to a device for detecting a magnetic field in the vicinity of such an implant.

2. Description of the Prior Art

In a medical implant, such as a pacemaker, a magnetic field detector is used for non-invasive activation of different functions in the implant in combination with a permanent magnet placed in the vicinity of the implant at the outside of the patient's body. Some of the functions which can be activated in, e.g., a pacemaker are: disabling the pacemaker's demand function so the pacemaker adapts its operation to battery capacity and having the pacemaker operate in a special, temporary stimulation mode, e.g., in the case of tachycardia, and in conjunction with pacemaker programming.

Outside the implant art, the detection of magnetic fields in a number of different ways, e.g., with the aid of reed switches, by changing the resonance frequency or inductance, etc., is generally known.

One device for determining the strength of a magnetic field is described in an article by Lennart Grahm, "Elektrisk mätteknik, Analoga instrument och mätmetoder," part 2, 1977, Elektrisk mätteknik, Lund, pp. 543–545. As described therein, the voltage induced in a small test body made of ferromagnetic metal is examined with a Förster probe. The Förster probe consists of a small test body made of a ferromagnetic material with high permeability and provided with two windings, one of which is used for alternating current magnetization and the other is used for measuring the ensuing induced voltage. The larger the constant magnetic field, the greater the amplitude of even harmonics when the probe is placed in a constant magnetic field. Thus, a phase detector with a reference voltage equal to twice the frequency of the excitation current can be used for supplying a signal which increases with an increase in the constant magnetic field.

In the implant art, a conventional magnetic field detector consists of a reed switch. Reed switches, however, are sensitive and rather expensive components which also occupy a relatively large amount of space in the implant.

In order to eliminate the need for a reed switch, therefore, recent proposals have suggested utilization of the implant's telemetry unit so that the unit can also be used for detecting the presence of a magnetic field, in addition to its telemetry function.

U.S. Pat. No. 4,541,431 discloses one such proposal with a combined telemetry and magnetic field detector unit. This unit contains a conventional resonant circuit containing, e.g., a coil used in telemetry for transmitting and receiving data. The resonant circuit is also used for sensing the presence of a magnetic field whose strength exceeds a predefined value. The resonant frequency for the resonant circuit varies with the strength of the magnetic field. The resonant circuit is periodically activated, and the number of zero crossings of its signal with a sensing window with a predefined duration is determined. If a predetermined number of zero crossings occurs, this means that the strength of the magnetic field exceeds the predefined value.

Thus, the known unit requires a number of components for detecting the frequency deviation, and thus the magnetic field.

SUMMARY OF THE INVENTION

An object of the present invention is to provide a simplified and improved device for detecting magnetic fields in the vicinity of an implant.

The above object is achieved in accordance with the principles of the present invention in a combined magnetic field detector and telemetry unit for use in a medical implant, having a telemetry circuit connected to a voltage source, control logic which generates control signals respectively indicating operation in a telemetry mode or in a magnetic field detection mode, a coil unit formed by a plurality of coil unit parts, and a plurality of switches, which are individually controlled by the control logic in order to configure the electrical connections of the coil unit parts so that the coil unit can be used, with different configurations, in the telemetry mode and in the magnetic field detection mode. In the telemetry mode, selected switches are closed so as to connect the coil unit into the telemetry circuit, the coil unit with the telemetry circuit thereby being able to receive and transmit telemetry signals. In the magnetic field detection mode, selected switches are closed so as to connect the coil unit parts in a manner forming a pulse transformer having a primary side and a secondary side. The pulse transformer generates an output signal having a characteristic, such as its amplitude, which varies dependent on the presence of a magnetic field. The output of the pulse transformer is supplied to a magnetic field indicator connected to the secondary side of the pulse transformer, which generates a signal indicating the presence of a magnetic field when the characteristic satisfies a predetermined condition, such as by exceeding a predetermined threshold.

According to the invention, the reed switch is eliminated, in contrast to the solution proposed in the aforementioned U.S. Pat. No. 4,541,431, by the use of a pulse transformer for magnetic field detection, whereby the pulse transformer is devised so it can also be used for the implant's telemetry function.

With a pulse transformer, magnetic field detection is performed by determining the change in the pulse transformer's response to an applied pulse. This can be achieved simply and with few components, and the reliability of detection accordingly increases simultaneously.

Further embodiments of the invention include a version, in which, e.g., the threshold value for magnetic field detection is programmable.

DESCRIPTION OF THE DRAWINGS

FIG. 1 is a block diagram of an implant incorporating a magnetic field detector of the invention.

FIG. 2 is a block diagram of a combined telemetry and magnetic field detector unit, constructed in accordance with the principles of the present invention.

DESCRIPTION OF THE PREFERRED EMBODIMENTS

Figure 3:
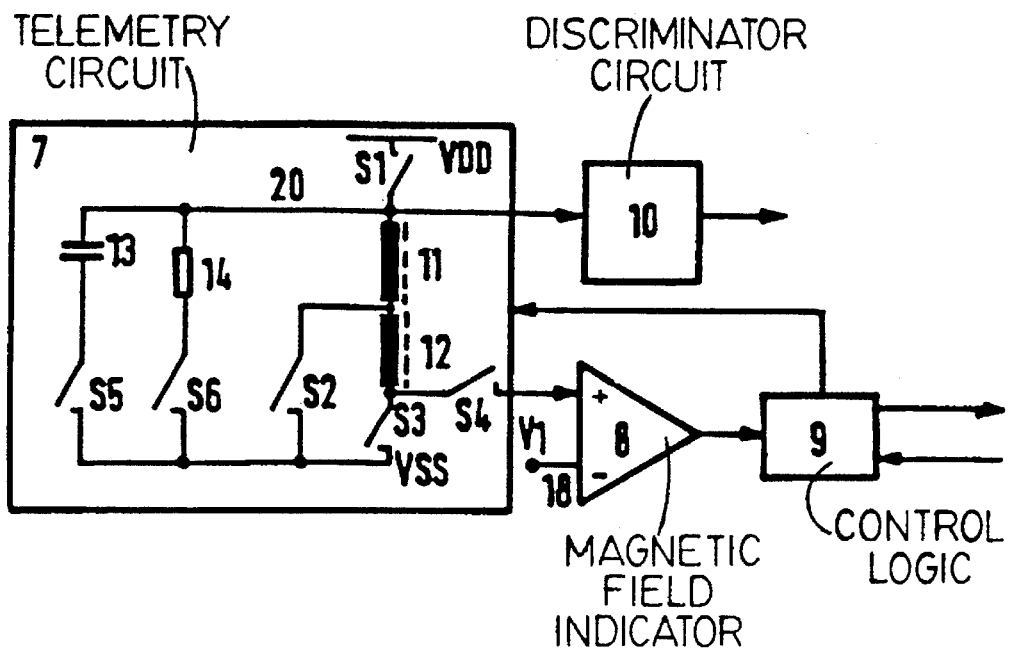
FIG. 3 is a schematic circuit diagram of a first embodiment of the invention.

In the FIGS. 1–6 the same reference designations are used for similar or identical elements.

The invention is primarily exemplified in the following description by an implant in the form of a pacemaker. It will be clear to anyone well-versed in the art, however, that no limitation is to be assumed by virtue of this exemplary context, and the implant can also be, e.g., a defibrillator, an insulin pump or any other medical device.

FIG. 1 shows an implant 1 inserted under the skin (designated with a dashed line in the FIG. 1). The implant 1 is connected to an organ 6 and is in communication with a programmer 4. The implant 1 contains a telemetry unit for duplex communications with the programmer 4, a programmable control device 3 for controlling and coordinating the units in the implant and a therapy unit 5 for supplying appropriate therapy to the organ 6, all in accordance with the prior art in the field. As previously noted, the implant 1 can be exemplified as a pacemaker, the organ 6 then being a heart and the therapy unit 5 a pulse generator, controlled by the control unit 3, for stimulating the heart 6 with stimulation pulses at a rate which can be set by a physician and transmitted to the implant using the programmer 4.

FIG. 2 is a block diagram of the telemetry unit 2.

According to the invention, this telemetry unit 2 is a combined telemetry and magnetic field detector unit and contains a telemetry circuit 7 used for transmitting and receiving signals to and from the programmer 4 and for detecting magnetic fields, a magnetic field indicator 8 which indicates the presence of a magnetic field, control logic 9 for controlling the telemetry unit 2, and a discriminator circuit 10 for signals received by the telemetry circuit 7. The function of the parts in the telemetry unit 2 will be apparent from the description below.

FIG. 3 shows in greater detail a first embodiment of the invention, wherein the telemetry circuit 7 contains a coil unit consisting of a first coil 11 and a second coil 12, connections to a drive voltage source $V_{DD}$ and a ground level $V_{SS}$, a capacitor 13, a resistor 14 and a connection point 20. By means of a plurality of switches S1–S6 controlled by the control logic 9, the components in the telemetry circuit are enabled according to the function the telemetry circuit is to perform.

The drive voltage source $V_{DD}$, is connected, via a switch S1 to the connection point 20. The first coil 11 and the second coil 12 are connected in series, with the first coil 11 being connected to the connection point 20 and the second coil 12 being connected, via a switch S3, to $V_{SS}$. The capacitor 13 is connected to the connection point 20 and, via a switch S5, to $V_{SS}$. The resistor 14 is connected to the connection point 20 and, via a switch S6, to $V_{SS}$.

The connection between the coils 11 and 12 is connected, via a switch S2, to $V_{SS}$. Between S3 and the second coil 12 there is a connection, via a switch S4, to the first input terminal of the magnetic field indicator 8. The discriminator circuit 10 is connected to the connection point 20.

Figure 4:
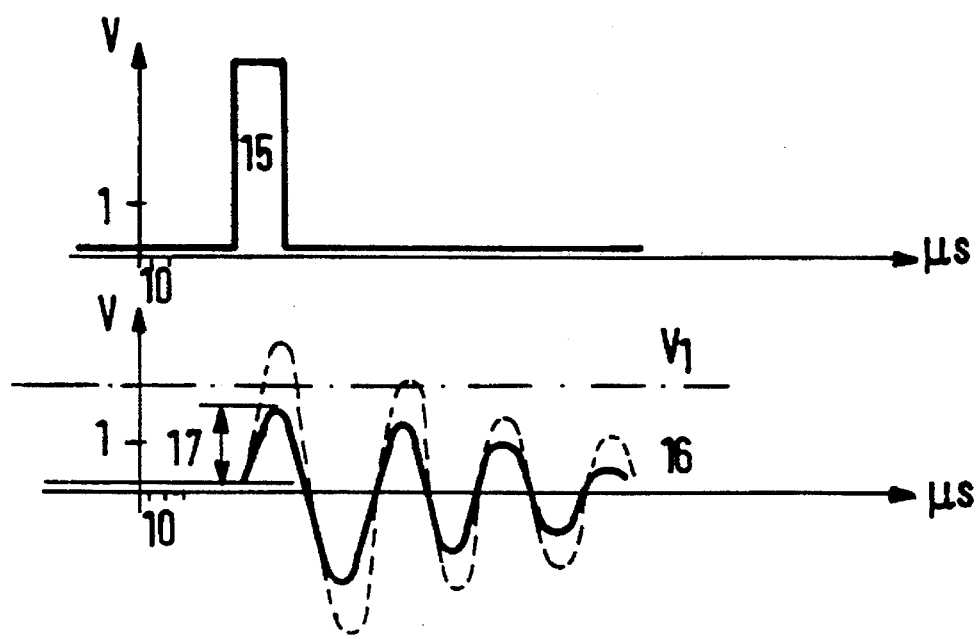
FIG. 4 shows a number of curve morphologies for the coil signals in the first embodiment.

The device senses at a specific interval, e.g. once a second, whether a magnetic field is present. When this magnetic field test is performed, the switches S2 and S4 are closed, whereas S3, S5 and S6 are open. Thus, the second coil 12 is connected by switch S4 to the magnetic field indicator 8. The indicator consists of a differential amplifier with a second input terminal 18 at which the desired threshold value for magnetic field detection is set. The setting can be made by telemetry from the programmer 4. The switch S1 is closed for a specific period of time, e.g. of about 30 μs. In this period, the first coil is therefore connected to the drive voltage $V_{DD}$, causing a brief pulse 15 to be applied to the first coil 11 (see FIG. 4). A signal 16 is thereby induced in the second coil 12, which is inductively coupled to the first coil 11. The coils 11 and 12 are wound on a common core and jointly form a pulse transformer. FIG. 4 shows certain curve morphologies for signals in the coils 11 and 12, without (dashed line) and with (solid line) an external magnetic field. In FIG. 4, the horizontal axis represents a time axis, graduated in μs, whereas the vertical axis represents voltage and is graduated in volts. If an external magnetic field is present, the permeability of the common core decreases. This leads in turn to a decrease in the mutual inductance between the coils 11 and 12. This can be seen in the curve morphology for the second coil 12 which displays a reduced initial amplitude 17 (the peak amplitude of the first half-period) when an external magnetic field is present. This initial amplitude is compared in the magnetic field indicator 8 with a first threshold value $V_1$, set in the magnetic field indicator 8. The magnetic field indicator 8 generates an output signal indicating when the initial amplitude drops below the value $V_1$, thereby providing an indication of the presence of a magnetic field. A typical value for $V_1$ can be 20% below the amplitude obtained when no magnetic field is present.

When the device is to be used for telemetry, the switches S2 and S4 are open, whereas S3 is closed. S5 is closed in transmission, i.e. the capacitor 13 is connected to $V_{SS}$, whereas S6 is open, i.e. the resistor 14 is not connected to $V_{SS}$. The coils 11 and 12 jointly form, with the capacitor 13, a resonant circuit which, with a suitable choice of component values, has a preferred resonant frequency of 8 kHz and a high Q. The switch S1 is quickly opened and closed, causing brief pulses to be applied to the resonant circuit in which the coils constitute the transmission antenna for the electromagnetic waves. The pulse trains generated in this manner contain the information to be transmitted to the programmer 4.

When signals are received from the programmer 4, S1 and S5 are open and S6 is closed. The coils 11 and 12 pick up the signals transmitted by the programmer 4, and these signals are sent to the control device 3 via the discriminator circuit 10. The discriminator circuit 10 contains, e.g., a comparator in which the signal level for the received signal is compared to a predefined threshold level, and only signals exceeding this level are processed. In reception, the resistor 14 damps the signal so that no residual voltage remains in the coils 11 and 12 when transmission or reception is to start.

Figure 5:
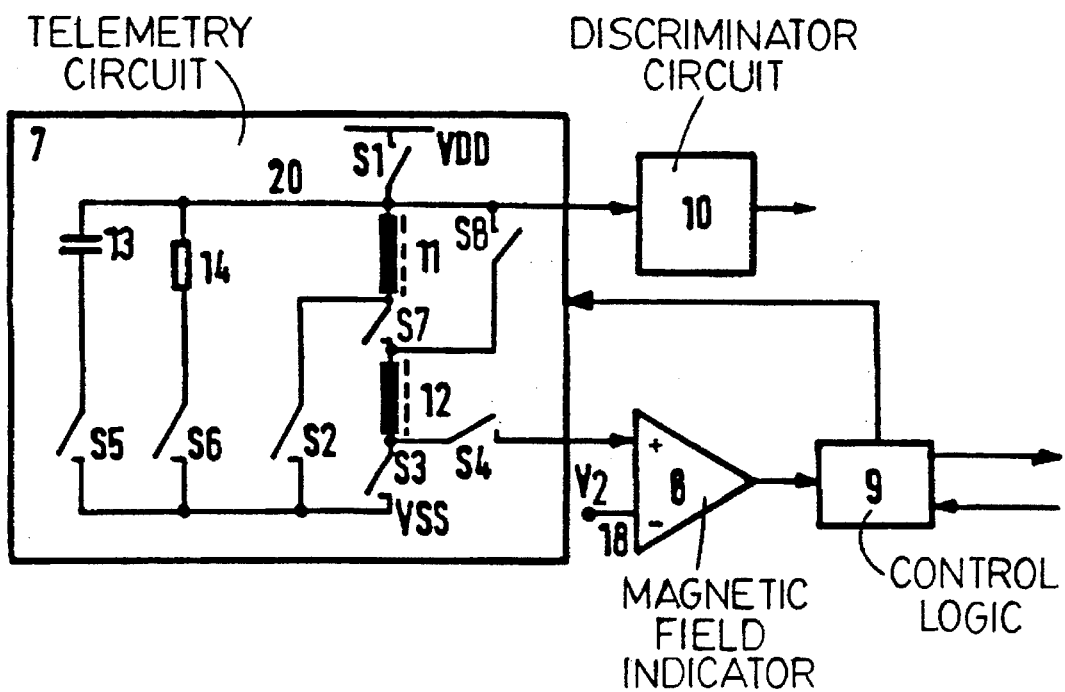
FIG. 5 is a schematic circuit diagram of a second embodiment of the invention.
Figure 6:
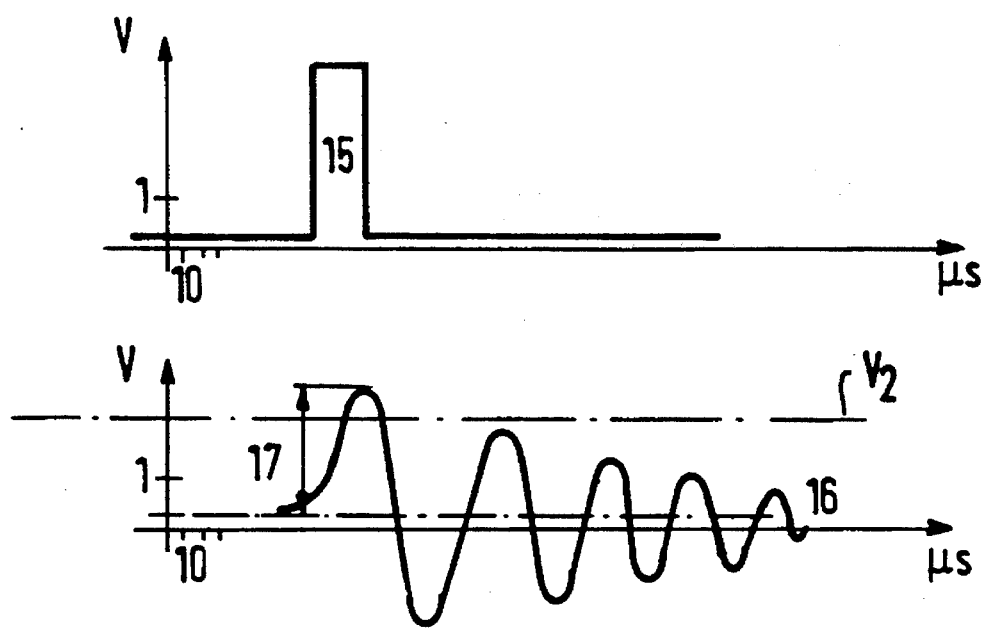
FIG. 6 shows a number of curve morphologies for the coil signals in the second embodiment.

Referring to FIGS. 5 and 6, a second preferred embodiment for the telemetry circuits 7 will now be described. Exactly as in the first preferred embodiment, these circuits contain a first coil 11 and a second coil 12 wound around the same core, a capacitor 13, a resistor 14, a connection point 20, a drive voltage $V_{DD}$ and a ground level, $V_{SS}$. Using a plurality of switches S1–S8, which are controlled by the control logic 9, the respective components are enabled according to the function the telemetry circuits are to perform. The switches S1 to S6 have the same placement and function as previously described. In addition, the first coil 11 is connected, via a switch S7, to the second coil 12, and the connection point 20 is connected, via a switch 8, to the connection between the switch S7 and the second coil 12. The switch S7 is located between the connection socket which is connected to $V_{SS}$ via S2, and the connection socket is connected to the connection point 20 via S8.

The device senses at a specific interval, e.g. once a second, whether any magnetic field is present. When this magnetic field test is performed, the switches S2, S4 and S8 are closed, whereas S3, S5, S6 and S7 are open. Thus, the second coil 12 is connected by switch S4 to the magnetic field indicator 8. The switch S1 is closed for a specific period of time, whereby a pulse 15 is emitted, in the same way as previously described, and applied to the first coil 1, and a signal 16 is induced in the second coil 12, the coils 11 and 12 jointly forming a pulse generator. FIG. 6 shows curve morphologies for signals on the coils 11 and 12, without (dashed line) and with (solid line) an external magnetic field. FIG. 6 uses the same designations for the axes as in FIG. 4. If no external magnetic field is present, the signal in the second coil 12 does not change when a pulse 15 is applied to the first coil 11 (if coils 11 and 12 are electrically equal). If a magnetic field is present, however, the curve morphology for the second coil will display a rising initial amplitude 17. Comparing this initial amplitude in the magnetic field indicator 8 with a second threshold value $V_2$, set in the magnetic field indicator 8 indicates when the initial amplitude exceeds the value $V_2$ and results in an output signal indicating the presence of a magnetic field.

When the device of FIG. 5 is to be used for telemetry, the switches S2, S4 and S8 are open, whereas S3 and S7 are closed. Telemetry transmission is otherwise performed in the same way as described above for the first embodiment.

The coil unit formed by coils 11 and 12 thus consists of two parts which for magnetic field detection, are interconnected by the control logic 9 in such a way that they form the respective primary side and secondary side of a pulse transformer. In the described, preferred embodiments, the primary side consists of the first coil 11 and secondary side of the second coil 12. In other embodiments, not shown herein, the primary side and secondary side respectively can consist of two or more coils.

In the two described embodiments, the coils 11 and 12 are connected in series when the device is used for telemetry. In other embodiments of the invention, the coils can be connected in parallel, or only one of the coils can be is utilized for telemetry.

There is no magnetic field detection while telemetry is in progress.

The threshold values $V_1$ and $V_2$ with which the initial amplitude of the signal at the second coil is compared can, as noted above, be set by telemetry when the implant is in place in a patient's body, or during implant fabrication.

Although modifications and changes may be suggested by those skilled in the art, it is the intention of the inventors to embody within the patent warranted hereon all changes and modifications as reasonably and properly come within the scope of their contribution to the art.

We claim as our invention:

1. A combination magnetic field detector and threshold unit for use in a medical implant, comprising:

a telemetry circuit connected to a voltage source;

control logic which generates control signals respectively for telemetry and magnetic field detection;

a coil unit including a plurality of coil unit parts;

switch means, controlled by said control logic for, when said control logic generates a control signal for telemetry, electrically connecting said coil unit into said telemetry circuit for forming means for receiving and transmitting telemetry signals and for, when said control logic generates a control signal for magnetic field detection, electrically connecting said coil unit parts for forming a primary side and a secondary side of a pulse transformer which generates an output signal having a characteristic which varies dependent on the presence of a magnetic field; and magnetic field indicator means, connected to said secondary side of said pulse transformer, for generating a signal indicating the presence of a magnetic field when said characteristic satisfies a predetermined condition.

2. A combined magnetic field detector and telemetry unit as claimed in claim 1 wherein said plurality of coil unit parts comprise a first coil and a second coil, and wherein said switch means comprises means for connecting said first coil as said primary side of said pulse transformer and for connecting said second coil as said secondary side of said pulse transformer.

3. A combined magnetic field detector and telemetry unit as claimed in claim 2 further comprising a common core on which both said first coil and said second coil are wound.

4. A combined magnetic field detector and telemetry unit as claimed in claim 2 wherein said switch means includes a first switch connected between said second coil and said magnetic field indicator means, said first switch being closed by said control logic by said control signal for magnetic field detection.

5. A combined magnetic field detector and telemetry unit as claimed in claim 4 wherein said switch means includes a second switch connected between said first coil and said voltage source, said second switch being briefly closed by said control signal for magnetic field detection and thereby causing said first coil to induce said second coil to produce said output signal.

6. A combined magnetic field detector and telemetry unit as claimed in claim 5 wherein said output signal comprises a resonant signal having an initial amplitude, and wherein said magnetic field indicator means comprises means for generating said signal indicating the presence of a magnetic field when said initial amplitude is less than a threshold value.

7. A combined magnetic field detector and telemetry unit as claimed in claim 5 wherein said first and second coils are connected in series, wherein said telemetry circuit includes a ground level, a resistor, a capacitor, and a connection point to which one side of each of said capacitor and said resistor, and said first coil and said second switch, are connected, and wherein said switch means includes a third switch via which said second coil is connected to ground level, a fourth switch via which the other side of said capacitor is connected to ground level, a fifth switch via which the other side of said resistor is connected to ground level, and a sixth switch via which said second coil is connected to ground level, said control signal for magnetic field detection closing said first and sixth switches and opening said third, fourth and fifth switches.

8. A combined magnetic field detector and telemetry unit as claimed in claim 7 wherein said switch means further includes a seventh switch connected in series between said first and second coils, and an eighth switch via which said second coil is connected, said control signal for magnetic field detection closing said first, sixth and eighth switches and opening said third, fourth, fifth and seventh switches.

9. A combined magnetic field detector and telemetry unit as claimed in claim 8 wherein said output signal induced in said second coil is a resonant signal having an initial amplitude, and wherein said magnetic field indicator means comprises means for generating said signal indicating the presence of a magnetic field when said initial amplitude exceeds a predetermined threshold.

10. A combined magnetic field detector and telemetry unit as claimed in claim 1 wherein said control logic comprises means for periodically generating said control signal for magnetic field detection.

11. A combined magnetic field detector and telemetry unit as claimed in claim 1 wherein said magnetic field indicator means comprises means, when said control logic generates said control signal for telemetry, for receiving a telemetry signal which sets said predetermined condition.

12. A combined magnetic field detector and telemetry unit as claimed in claim 1 wherein said magnetic field indicator means comprises a comparator having a predetermined threshold, said comparator generating said signal indicating the presence of a magnetic field dependent on a value of said characteristic relative to said predetermined threshold.

* * * * *